(12) United States Patent
Daicho

(10) Patent No.: US 6,793,943 B2
(45) Date of Patent: Sep. 21, 2004

(54) HEALTH FOOD PRODUCTS

(75) Inventor: Takao Daicho, Shida-gun (JP)

(73) Assignee: Daicho Kikaku Incorporated Company, Shizuoka (JP)

( * ) Notice: Subject to any disclaimer, the term of this patent is extended or adjusted under 35 U.S.C. 154(b) by 0 days.

(21) Appl. No.: 09/828,798

(22) Filed: Apr. 10, 2001

(65) Prior Publication Data

US 2002/0076451 A1 Jun. 20, 2002

(30) Foreign Application Priority Data

Oct. 20, 2000 (JP) .......................... 2000-321238
Nov. 10, 2000 (JP) .......................... 2000-343606
Dec. 27, 2000 (JP) .......................... 2000-397334

(51) Int. Cl.$^7$ .............................. A61K 35/78; C07J 9/00
(52) U.S. Cl. ........................ 424/725; 424/757; 552/549; 536/8
(58) Field of Search .............................. 424/757, 195.1, 424/725; 536/8; 552/549

(56) References Cited

U.S. PATENT DOCUMENTS 4,487,766 A * 12/1984 Mach .......................... 424/180
5,904,924 A    5/1999 Gaynor et al.
6,280,776 B1 * 8/2001 Sha et al. .................... 424/728

FOREIGN PATENT DOCUMENTS

| GB | 976096 | | 11/1964 |
|----|--------|---|---------|
| JP | 57063057 | * | 4/1982 |
| JP | 04-159226 A | | 6/1992 |
| JP | 411046719 A | * | 2/1999 |
| WO | WO 00/59523 | | 10/2000 |

OTHER PUBLICATIONS

Sigma Catalog, 1997. p. 280.*
Michael R. Peluso et al. "A Cooperative Interaction Between Soy Protein and its Isoflavone–Enriched Fraction Lowers Hepatic Lipids in Male Obese Zucker Rates and Reduces Blood Platelet Sensitivity in Male Sprague–Dawley Rats" Nutrient Interaction and Toxicity, pp. 2333–2342, 2000.
"Chinese Medical Science Expected by the People–Methodology for Scientific Way of Thinking Thereof–", Chinese Journal of Information on Traditional Chinese Medicine, vol. 6, No. 4, pp. 3–4, Apr., 1999 (w/ English Translation).
Wang Chunfang et al., *Quantitative Determination of Cholic Acid in Niuhuagquingxin Pill by TLC–Densometry*, Chinese Journal of Experimental Traditional Medicine Formulae, Dec. 1997, at 11, English Abstract.

* cited by examiner

Primary Examiner—Patricia Leith
(74) Attorney, Agent, or Firm—Oliff & Berridge, PLC

(57) ABSTRACT

An object of the present invention is to provide a very effective health food exhibiting the effect near that which has been already achieved by the traditional Chinese medical science. The present invention relates to a health food product comprising cholic acid, especially to a health food product comprising cholic acid and isoflavone and/or isoflavone glycoside.

6 Claims, No Drawings

HEALTH FOOD PRODUCTS

TECHNICAL FIELD

The present invention relates to novel health food products. The present invention relates to novel nutritional food products useful for providing effective elements to a health conscious population.

BACKGROUND OF THE INVENTION

One of the bases of the traditional Chinese medical science is to keep the human body in a normal state at all times. There has been a concept called "Ki-Ketsu-Sui (vital energy-blood-water)" in order to achieve such an object. Further, concrete means and methods have been known already based upon the said concept.

However, the concept has been explained with a philosophical expression peculiar to China. The means and methods therefor are based on applications of products which are prepared by drying naturally-occurring materials only. Since those are the concept which is hardly understood and the means/methods which are hardly accepted in the world of scientific culture, such a precise traditional Chinese medical science has been rarely utilized outside China.

In the meanwhile, an article entitled Chinese Medical Science Expected by the People—Methodology for Scientific Way of Thinking Thereof was reported in Chinese Journal of Information on Traditional Chinese Medicine, Vol. 6, No. 4, April, 1999 (which is one of the authorized medical journals published in China). In this article, the portions related to science covered by the concept of "Ki-Ketsu-Sui" have been explained using scientific terms which are the common languages throughout the world.

Thus, the science covered by the concept of "Ki-Ketsu-Sui" is briefly explained as follows:

(1) the science covered by the term "Ki (vital energy)" refers to those steadily operating all functions inherent in human bodies, (2) the science covered by the term "Ketsu (blood)" refers to those supplying a substance necessary for achieving such functions via blood vessels into the body, and (3) the science covered by the term "Sui (water)" refers those well supplying such a necessary substance carried via the blood vessels to a site where there is no blood vessel as well, provided that the route for the necessary substance at that time is a water flow formed from the inside to the outside of the body.

As shown in the case where a large number of already-existing scientific theories have been infinitely developed as a result of their advent, the fact that entirely new scientific concept has been expressed as the medical theory included in the traditional Chinese medical science leads to a supply of new medical means to the world of the Western medical science. It firstly provides a possibility that we will be able to practice prevention of diseases, potentiation of natural healing power and acceleration of recovery after the disease, which have been available merely as the terms even in the Western medical science up to now.

In addition, this new medical theory markedly facilitates the determination of effective ingredients necessary for achieving the medically theoretical part, which ingredients are contained in each of crude drugs used as materials in the traditional Chinese medical science. As a result, it enables us to convert all materials used for practice of this new medical theory into effective and active ingredients with high purity.

The most important requirement for health foods which all the people can utilize is at least less expensive in view of product's price than multi-vitamin drugs which are currently available in the market.

SUMMARY OF THE INVENTION

The present inventor has found that cholic acid is an effective component for guaranteeing the in vivo transport of substances necessary for achieving the functions of human body via blood vessels.

The present inventor has also found that isoflavones and isoflavone glycosides, particularly soybean isoflavones and soybean isoflavone glycosides, have an action of accelerating the in vivo water flow which is a means for supplying substances (carried by blood vessels) necessary for achieving the functions to various body parts where no blood vessels run.

Further, the present inventor has found that cholic acid is admixed with at least one member selected from isoflavones and isoflavone glycosides, especially soybean isoflavones and soybean isoflavone glycoside, to afford an excellent health food with a synergistic effect.

An object of the present invention is to provide, based upon such a new theory, very effective health foods each exhibiting the effect near that which has already been achieved by the traditional Chinese medical science from ancient times.

The present invention relates to health food products each comprising cholic acid, in particular to health food products each comprising cholic acid in admixture with isoflavone and/or isoflavone glycoside.

DETAILED DESCRIPTION OF THE INVENTION

The health food products of the present invention may be ingested by any means. Because all healthy people desire to prevent diseases, natural healing power is a force which is achieved by patient's body per se for all diseases whereby all patients desire to achieve the natural healing power, together with the conventional Western medical therapy, and all post-diseased people released from the Western medical symptoms desire the recovery after the disease, it is desirable that the health food products of the present invention are ingested on a daily basis.

The particularly preferable isoflavone includes soybean isoflavones comprised in soybean. The particularly preferable isoflavone glycoside includes soybean isoflavone glycosides comprised in soybean.

The daily dose of cholic acid is preferably 1 to 1000 mg, more preferably 2 to 300 mg, and most preferably 10 to 100 mg. The daily dose of isoflavone is preferably 1 to 500 mg, more preferably 5 to 200 mg, and most preferably 10 to 100 mg. The daily dose of isoflavone glycoside is preferably 1 to 500 mg, more preferably 5 to 200 mg, and most preferably 10 to 100 mg.

In accordance with the present invention, it is allowable that the health food product contains cholic acid, preferably both cholic acid and isoflavone and/or isoflavone glycoside. It is also allowable that the health food product is in admixture with other ingredients including vitamins, heme Fe, prune extracts (*Prunus Domestica* fruit extracts), crude drugs or vegetable and animal drugs (galenicals; "SHOU-YAKU" as pronounced in Japanese) including those capable of activating or stimulating the functions of organs, glands and blood vessels, all controlled by autonomic nerves, those capable of aiding digestion, and others.

The crude drugs of 10 or more kinds have been known as those capable of activating or stimulating the functions of organs, glands and blood vessels, all controlled by autonomic nerves. Examples of such crude drugs are ginseng (*Ginseng Radix, Panax Ginseng*), etc. Some of active elements have been revealed for not only ginseng but also such crude drugs.

Accordingly, such active elements can be preferably admixed therewith. The admixture of such active elements will lead to achievement of activating body-functions.

The particularly preferable crude drugs include Ginseng (*Panax Ginseng* or *Ginseng Radix*), *Codonopsitis Radix, Psuodostellariae Radix*, American Ginseng, *Astragali Radix, Atractylodis Rhizoma, Dioscoreae Rhizoma*, Glycyrrhia (*Glycyrrhizae Radix*), Jujube Fruit (*Zizyphi Fructus, Zizyphus vulgaris*), Dulcium (malt sugar derived from Oryza seed), *Polygonati Rhizoma, Codonopis Ianccolata* Benth et Hock fil.

The particularly preferable crude drugs capable of aiding digestion include *Crataegi Fructus, Massa Medicata Fermentat, Raphani Semen, Fructus Hordei Germinatus, Fructus Oryzae Germinatus,* (*Oryza sativa* L.), *Galli Stomachichum Corium, Asa Foetida*, etc.

The health food products of the present invention can be eaten as conventional forms including powdery, solid, and liquid forms. Materials for admixture include lactose, starch, vegetable oil, etc.

Biles of livestock such as cattle and pigs comprise taurocholic acid which can be hydrolyzed to form taurine. Taurine is in great demand for starting materials in oder to prepare foods and its production is high. In its production process, cholic acid as used herein is also produced in large amounts. This production of cholic acid is more than enough to use as a source for reagents. Most of cholic acid are treated as industrial wastes and are therefore extremely inexpensive.

Other materials as used herein include isoflavones and isoflavone glycosides.

The active elements contained in soybean are several species of isoflavone glycosides including daidzin, glycitin, genistin, etc. and aglycons thereof, i.e., several species of isoflavones including daidzein, glycitein, genistein, etc.

The soybean is a starting material for producing soybean oil. There is a great demand for soybean oil. Therefore, large amounts of soybean oil are manufactured together with large amounts of by-products, soybean cakes. Although part of such soybean cakes are employed as sources for preparing soybean proteins, etc. which are starting materials for food products, the soybean cake is mainly used for a fertilizer or feed for livestock and its price is therefore extremely low. The soybean cakes which are almost industrial wastes can be used as starting materials to produce inexpensively soybean isoflavones and soybean isoflavone glycosides with high purity.

EXAMPLES

Described below are examples of the present invention which are provided for illustrative purposes.

Cholic acid as used in examples is set to be 90% in purity. Soybean isoflavone glycoside as used in examples is set to be 40% in purity.

Example 1

Powders

Cholic acid 60 mg, soybean isoflavone glycoside 125 mg, lactose 2700 mg, cornstarch 1100 mg, light anhydrous silicic acid 5 mg, and magnesium stearate 10 mg (total 4000 mg, 2 g per powder paper, twice a day).

A formula except that soybean isoflavone glycoside was replaced with soybean isoflavone was blended to afford powders in the same fashion as above.

Example 2

Granular Forms

Cholic acid 60 mg, soybean isoflavone glycoside 125 mg, lactose 2700 mg, cornstarch 800 mg, crystalline cellulose 300 mg, light anhydrous silicic acid 5 mg, and magnesium stearate 10 mg (total 4000 mg).

A formula except that soybean isoflavone glycoside was replaced with soybean isoflavone was granulated to afford granules in the same fashion as above.

Example 3

Spherical Granules

Cholic acid 60 mg, soybean isoflavone glycoside 125 mg, lactose 515 mg, cornstarch 400 mg, *Prunus mume* fruit powders ("KAN-BAI-KO" as pronounced in Japanese) 500 mg, and crystalline cellulose 400 mg (total 2000 mg).

A formula except that soybean isoflavone glycoside was replaced with soybean isoflavone was granulated to afford spherical granules in the same fashion as above.

Example 4

Tablets

Cholic acid 140 mg, soybean isoflavone glycoside 280 mg, lactose 4000 mg, carboxymethylcellulose calcium 320 mg, hydroxypropylcellulose 74 mg, crystalline cellulose 700 mg, CARPLEX 30 mg, and magnesium stearate 10 mg (total 5554 mg, 280 mg per tablet, 5 tablets per dose, twice a day).

A formula except that soybean isoflavone glycoside was replaced with soybean isoflavone was compressed to afford tablets in the same fashion as above.

Example 5

Hard Capsules

Cholic acid 60 mg, soybean isoflavone glycoside 125 mg, cornstarch 959 mg, and magnesium stearate 9 mg (total 1153 mg, #1 capsule, 4 capsules a day).

A formula except that soybean isoflavone glycoside was replaced with soybean isoflavone was blended and packed to afford hard capsules in the same fashion as above.

Example 6

Soft Capsules

Cholic acid 60 mg, soybean isoflavone glycoside 125 mg, yellow beeswax 55 mg, and edible oil 960 mg (total 1200 mg, 4 capsules a day).

A formula except that soybean isoflavone glycoside was replaced with soybean isoflavone was blended and packed to afford soft capsules in the same fashion as above.

Example 7

Drink

Cholic acid 60 mg, soybean isoflavone glycoside 125 mg, ginseng extract 1500 mg, Euphoria longan extract 100 mg, shisandra fruit fluidextract 300 mg, royal jelly 150 mg, riboflavin sodium phosphate 10 mg, ethanol 1.2 ml, parahydroxybonzoic acid 4 mg, and purified water qs (total 50ml).

A formula except that soybean isoflavone glycoside was replaced with soybean isoflavone was mixed to afford drinks in the same fashion as above.

Example 8

Granules

Cholic acid 60 mg, soybean isoflavone glycoside 125 mg, thiamin hydrochloride 10 mg, pyridoxine hydrochloride 100 mg, hydroxocobalamin hydrochloride 1.027 mg, tocopherol acetate 100 mg, lactose 2700 mg, crystalline cellulose 300 mg, light anhydrous silicic acid 5 mg, magnesium stearate 10 mg, and cornstarch qs (total 4000 mg, 2 g per container, twice a day).

A formula except that soybean isoflavone glycoside was replaced with soybean isoflavone was granulated to afford granules in the same fashion as above.

Example 9

Capsules

Cholic acid 60 mg, soybean isoflavone glycoside 125 mg, vitamin A oil 4 mg, cholecalciferol 0.005 mg, tocopherol acetate 10 mg, vitamin C 600 mg, crystalline cellulose 250 mg, magnesium stearate 6 mg, and cornstarch qs (total 1150 mg, #1 capsule, 4 capsules a day).

A formula except that soybean isoflavone glycoside was replaced with soybean isoflavone was blended and packed to afford capsules in the same fashion as above.

An object of the present invention is to keep the body in a normal state so as to prevent a disease, to promote natural healing power to the disease, and to accelerate the recovery after the disease. However, in order to collect the medical data therefor, it is necessary not only to test several ten thousand patients but also to take a long period which is nearly as long as one's life and therefore its realization is extremely difficult.

As a result of a preliminary administration experiment, it was noted in several persons who ingested cholic acid alone that troubles by drinking an alcoholic beverage were ameliorated (presumably related to the science of "Ketsu") while it was characteristically noted in several persons who ingested soybean isoflavone alone or soybean isoflavone glycoside alone that an evacuation was improved (presumably related to the science covered by "Sui").

Further, in order to prove the advantage of the joint use of both the elements, three kinds of samples:

(a) a sample of cholic acid alone,
(b) a sample of soybean isoflavone glycoside alone, and
(c) a sample of cholic acid in admixture with soybean isoflavone glycoside, were each administered for 2 months to each group containing 30 persons to be tested. The results were investigated.

The results are shown in Table as follows:

TABLE

|  | Alcoholic beverage tasted good | No hangover noted | Feces amount increased | Evacuation became easy | Significantly recovered from fatigue |
|---|---|---|---|---|---|
| soybean isoflavone glycoside group | 2 Persons | 1 Person | 5 Persons | 3 Persons | No Person |
| cholic acid | 8 Persons | 4 Persons | No Person | 1 Person | No Person |
| cholic acid + soybean isoflavone glycoside group | 25 Persons | 23 Persons | 26 Persons | 20 Persons | 28 Persons |

(numbers of the persons)

As apparent from this Table, when cholic acid was admixed with soybean isoflavone glycosides, most of the administered persons showed a significant recovery from fatigue. Such results show that cholic acid can be orally administered in admixture with soybean isoflavone glycosides with a new efficacy which was not noted in the case of a sole use of each single component, as compared with the sole use of each of soybean isoflavone glycosides and cholic acid.

For soybean isoflavones, it is ascertained that an efficacy thereof similar to that of soybean isoflavone glycosides was obtained.

Such results as noted in the Table show that the two components can be admixed together to achieve synergistically each efficacy of the two components.

Although it is hard to fully interpret the results in the above Table because an effect through the traditional Chinese medical science sometimes surpasses the ability of science, the data are understandable even when checked from a scientific view only.

Thus, it was mentioned already that cholic acid has an action of carrying the substance necessary for achieving the functions in various sites of human body through the blood vessel and soybean isoflavones and soybean isoflavone glycosides have an action of transporting it to sites (such as tissues and body fluid) in which blood vessel is not available and which is beyond the blood vessel, including spaces (occupying most of the human body) which are far more than the volume occupied by blood vessels. If either of the two is inhibited or if either of both actions thereof is merely activated, it is not possible to convey the substances necessary for achieving the function to all areas of the human body.

A quick ameliorating efficacy on various diseases is not due to an achievement of the direct therapeutic action on each disease but it is due to the fact that either the disease naturally cures because the human body comes near the normal state or the body achieves the natural healing power to try to fundamentally cure the disease. Thus, unlike in the Western medical science, it is not the result due to an achievement of the limited action directed to the only one aspect of the disease.

According to the new medical theory covered by the "Ki-Ketsu-Sui" of the traditional Chinese medical science, it is now expected that either each effective ingredient of crude drugs having the action of "Ketsu" or a compound having such an action may be used together with either each effective ingredient of crude drugs having the action of "Sui" or a compound having such an action, thereby leading to synergistic potentiation of the action independently available by each ingredient or compound in the same way as the joint use of cholic acid in combination with isoflavones and/or isoflavone glycosides, particularly soybean isoflavone and/or soybean isoflavone glycoside, according to the present invention.

Advantages of the Present Invention

In accordance with the present invention, it is possible to achieve prevention of diseases, potentiation of natural healing power and acceleration of the recovery after diseases by means of food.

Further, cholic acid, which is one of essential elements for the present invention, can be produced in large amounts in the process of hydrolyzing taurocholic acid to form taurine. The production of cholic acid is more than enough to use as a source for reagents. Most of cholic acid are treated as industrial wastes and are therefore extremely inexpensive.

Similarly, soybean isoflavones and soybean isoflavone glycosides, which are one of essential elements for the present invention, are contained in soybean cakes which are by-products in the production processes of soybean oil. The soybean cakes are produced in large amounts together with large amounts of soybean oil. Although part of such soybean cakes are employed as sources for preparing soybean proteins, etc. which are starting materials for food products, the soybean cake is mainly used for a fertilizer or feed for livestock and its price is therefore extremely low. The soybean cakes which are almost industrial wastes can be used as starting materials to produce inexpensively soybean isoflavones and soybean isoflavone glycosides with high purity.

Accordingly, the present invention is very advantageous to the supply of extremely inexpensive health food products.

What is claimed is:

1. A health food product consisting of cholic acid at a daily dose of 1 to 1,000 mg and at least one member selected from the group consisting of isoflavones and isoflavone glycosides at a daily dose of 1 to 500 mg.

2. The health food product of claim 1, wherein the isoflavones are soybean isoflavones and the isoflavone glycosides are soybean isoflavone glycosides.

3. A health food product consisting of a vitamin, cholic acid at a daily dose of 1 to 1,000 mg and at least one member selected from the group consisting of isoflavones and isoflavone glycosides at a daily dose of 1 to 500 mg.

4. A health food product consisting of cholic acid at a daily dose of 1 to 1,000 mg and at least one member selected from the group consisting of isoflavones and isoflavone glycosides at a daily dose of 1 to 500 mg, and at least one member selected from the group consisting of Ginseng (*Panax Ginseng* or *Ginseng Radix; Panax ginseng* C.A. Mey.), *Codonopsitis Radix* (*Codonopsis pilosula* (Franch.) Nannf.), *Psuodostellariae Radix* (*Pseudostellaria heterophylla* (Mig.) Pax ex Pax et Hoffm.), American Ginseng (*Panax quinque folium* L.), *Astragali Radix* (*Aastragalus membranaceus* Bge.), *Atractylodis Rhizoma* (*Atractylodes macrocephala* Koidz. (*A. ovata* A.P.DC.)), *Dioscoreae Rhizoma* (*Dioscorea batatas* Decne.), Glycyrrhia (*Glycyrrhizae Radix; Glycrrhiaza uralensis* Fisch.), Jujube Fruit (*Zizyphi Fructus, Zizyphus vulgaris; Zizyphus jujuba* Mill.), Dulcium (malt sugar derived from Oryza seed; *Saccharum granorum*), *Polygonati Rhizoma* (*Polygonatum sibiricum* Red.), and *Codonopsis lanceolata* Benth. et Hock. fil.

5. A health food product consisting of cholic acid at a daily dose of 1 to 1,000 mg and at least one member selected from the group consisting of isoflavones and isoflavone glycosides at a daily dose of 1 to 500 mg, and at least one member selected from the group consisting of *Crataegi Fructus* (*Crataegus pinnatifida* Bge. rar. major N.E.Br., *Crataegus pinnatifda* Bge., and *Crataegus cuneata* Sieb. et Zucc.), *Massa Medicata Fermentat, Raphani Semen* (*Rophanus sativus* L.), *Fructus Hordei Germinatus* (*Hordeum vulgare* Linné), *Fructus Oryzae Germinatus* (*Oryza sativa* L.), *Galli Stomachichum Corium* (*Gallus gallus domesticus* Brisson), and *Asa Foetida* (*Ferula assafoetida* Regel).

6. A health food product consisting of a vitamin, cholic acid at a daily dose of 1 to 1,000 mg and at least one member selected from the group consisting of isoflavones and isoflavone glycosides at a daily dose of 1 to 500 mg.

* * * * *